(12) United States Patent
Kato (10) Patent No.: US 7,885,439 B2
(45) Date of Patent: Feb. 8, 2011

(54) APPARATUS AND METHOD FOR CREATING IDENTIFICATION INFORMATION BASED ON UNIQUE COMPONENTS OF A BODY

(75) Inventor: Yumi Kato, Tokyo (JP)

(73) Assignee: Sony Corporation, Tokyo (JP)

( * ) Notice: Subject to any disclaimer, the term of this patent is extended or adjusted under 35 U.S.C. 154(b) by 1179 days.

(21) Appl. No.: 11/052,912

(22) Filed: Feb. 9, 2005

(65) Prior Publication Data

US 2005/0215877 A1 Sep. 29, 2005

(30) Foreign Application Priority Data

Mar. 18, 2004 (JP) ............................. 2004-078391

(51) Int. Cl.
*G06K 9/00* (2006.01)
*A61B 5/05* (2006.01)

(52) U.S. Cl. ...................... 382/128; 600/407
(58) Field of Classification Search .................. 382/128
See application file for complete search history.

(56) References Cited

U.S. PATENT DOCUMENTS

| | | | | |
|---|---|---|---|---|
| 5,526,258 A | * | 6/1996 | Bacus ......................... | 382/129 |
| 5,623,528 A | * | 4/1997 | Takeda ........................... | 378/2 |
| 5,798,262 A | * | 8/1998 | Garini et al. .............. | 435/287.2 |
| 5,848,177 A | * | 12/1998 | Bauer et al. .................. | 382/128 |
| 5,889,881 A | * | 3/1999 | MacAulay et al. .......... | 382/133 |
| 5,970,182 A | * | 10/1999 | Goris .......................... | 382/278 |
| 6,018,565 A | * | 1/2000 | Ergun et al. .................... | 378/95 |
| 6,298,109 B1 | * | 10/2001 | Ergun et al. ..................... | 378/4 |
| 6,388,788 B1 | * | 5/2002 | Harris et al. ................ | 359/196 |
| 6,397,096 B1 | * | 5/2002 | Liu et al. .................... | 600/419 |
| 6,573,063 B2 | * | 6/2003 | Hochman .................... | 435/29 |
| 6,704,439 B1 | * | 3/2004 | Lee et al. .................... | 382/131 |
| 2002/0009213 A1 | * | 1/2002 | Rowe et al. ................. | 382/115 |
| 2002/0035329 A1 | * | 3/2002 | Kamiyama .................. | 600/458 |
| 2002/0048014 A1 | * | 4/2002 | Kono et al. ................... | 356/71 |
| 2002/0058874 A1 | * | 5/2002 | Ono et al. ................... | 600/476 |
| 2003/0170179 A1 | * | 9/2003 | Licha et al. ................. | 424/9.6 |
| 2004/0258285 A1 | * | 12/2004 | Hansen et al. .............. | 382/128 |

* cited by examiner

*Primary Examiner*—David P Rashid
(74) *Attorney, Agent, or Firm*—Oblon, Spivak, McClelland, Maier & Neustadt, L.L.P.

(57) ABSTRACT

An identification information creation apparatus and method capable of improving reliability in an identification process. A prescribed number or fewer isolated pixels are eliminated as condition noises from a binarized image created from images obtained by imaging blood vessels unique to a body, and identification information is created based on the blood vessels of the resultant noise-free binarized image. This can reduce a possibility of creating the identification information with the condition noises as a part of the blood vessels, thus making it possible to prevent the identification information from deteriorating due to different imaging conditions and physiologic change of imaging target and thus improving reliability in the identification process.

8 Claims, 7 Drawing Sheets

FIG.5A (A-1) RESULT OF ADDING AND AVERAGING 40 IMAGES (A-2) NO ADDITION/ AVERAGING PROCESS

FIG.5B (B-1) RESULT OF ADDING AND AVERAGING 50 IMAGES (B-2) NO ADDITION/ AVERAGING PROCESS

FIG.8A  EFFECT OF LIGHT

FIG.8B

APPARATUS AND METHOD FOR CREATING IDENTIFICATION INFORMATION BASED ON UNIQUE COMPONENTS OF A BODY

BACKGROUND OF THE INVENTION

1. Field of the Invention

This invention relates to an apparatus and method for creating information and, more particularly, is suitably applied to a case of creating identification information based on blood vessels of a body, for example.

2. Description of the Related Art

There has been proposed an identification apparatus which performs an identification process by using a formation pattern (hereinafter, referred to as blood vessel formation pattern) of blood vessels unique to a body.

Such the identification apparatus images unique components, or blood vessels of a registrant, extracts a blood vessel formation pattern from the resultant blood vessel image, and registers this pattern in a prescribed database. This imaging is performed by using such characteristics that light of a near-infrared light bandwidth is specifically absorbed in deoxygenization hemoglobin (venous blood) or oxygenation hemoglobin (arterial blood) existing in blood vessels.

Then, to identify the registrant, the identification apparatus extracts a blood vessel formation pattern of the same unique components in the same manner as the registration process, and compares the extracted blood vessel formation pattern to the blood vessel formation pattern being registered in the database (for example, refer to Japanese Patent Laid Open No. 2003-242492).

By the way, the identification apparatus extracts blood vessel formation patterns with different accuracy due to noises. The noises are generated due to different imaging conditions in an optical system, such as an irradiation amount and irradiation strength, and physiologic change of imaging target between the registration process and the identification process. As a result, a rightful user may not be identified as a registrant.

Further, if a user uses different imaging apparatuses for registration and identification, the imaging apparatuses extract blood vessel formation patterns with different accuracy due to noises which are unique to the solid imaging elements of the imaging apparatuses.

As described above, the conventional identification apparatuses have different accuracy in extracting a blood vessel formation pattern due to noises, resulting in an unreliable identification process.

SUMMARY OF THE INVENTION

This invention has been made in view of foregoing and intends to propose an apparatus and method for creating identification information, which are capable of improving reliability in an identification process.

To solve the above problems, this invention provides an information creation apparatus for creating information on a body. This apparatus comprises: an imaging means for imaging unique components of the body; a binarization means for creating a binarized image from an image received from the imaging means; an elimination means for eliminating a prescribed number or fewer isolated pixels from the binarized image received from the binarization means; and a creation means for creating identification information based on the unique components of the binarized image subjected to the elimination of the elimination means.

Further, this invention provides an information creation method for creating information on a body. This information creation method comprises: a first step of imaging unique components of the body; a second step of crating a binarized image from an image; a third step of eliminating a prescribed number or fewer isolated pixels from the binarized image created; and a fourth step of creating identification information based on the unique components of the binarized image subjected to the elimination.

According to this invention, noises generated due to different imaging conditions and physiologic change of imaging target can be eliminated. This can reduce a possibility of creating identification information with the noises as a part of blood vessels, resulting in preventing identification information from deteriorating due to the different imaging conditions and the physiologic change of imaging target and thus improving reliability in an identification process.

The nature, principle and utility of the invention will become more apparent from the following detailed description when read in conjunction with the accompanying drawings in which like parts are designated by like reference numerals or characters.

DETAILED DESCRIPTION OF THE EMBODIMENT

Preferred embodiments of this invention will be described with reference to the accompanying drawings:

(1) Construction of Identification Apparatus

Figure 1:
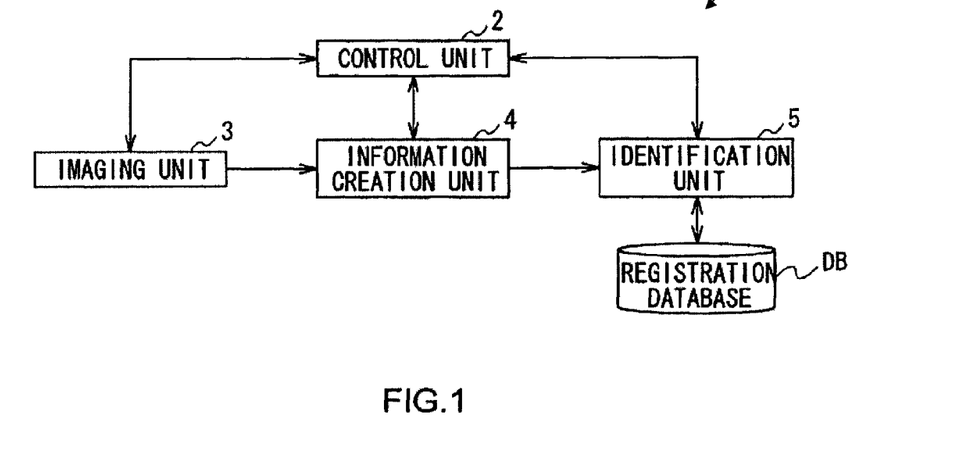
FIG. 1 is a block diagram of an identification apparatus according to this embodiment.

Referring to FIG. 1, reference numeral 1 shows a construction of an identification apparatus according to this embodiment. This identification apparatus 1 is composed of a control unit 2, an imaging unit 3, an information creation unit 4 and an identification unit 5, which are connected to each other.

The control unit 2 has a central processing unit, a work memory, an information memory, and a clock generator. The information memory stores plural kinds of data and programs.

The control unit 2 performs various processes by using various kinds of information being stored in the information memory and the clock generator, with a program being loaded in the work memory, thereby entirely controlling the identification apparatus 1 by sending control signals to the imaging unit 3, the information creation unit 4 and the identification unit 5.

By using such characteristics that light of a near-infrared light bandwidth is specifically absorbed in deoxygenization hemoglobin (venous blood) or oxygenation hemoglobin (arterial blood) existing in blood vessels, the imaging unit 3 images blood vessels of a body as an imaging target. The imaging unit 3 irradiates, for example, a finger, which is an imaging target, with near-infrared light to create a plurality of blood vessel images.

The information creation unit 4 creates a blood vessel formation pattern unique to the imaging target, based on the plurality of blood vessel images obtained as a result of imaging of the imaging unit 3, as data (hereinafter, referred to as blood vessel formation pattern data), and sends this to the identification unit 5.

The identification unit 5 is connected to a registration database DB via a prescribed transmission path. This registration database DB registers one or more blood vessel formation patterns which are created by performing the same process as the information creation unit 4 on results of imaging the same part with the imaging unit 3, as blood vessel formation patterns (hereinafter, referred to as registered blood vessel formation pattern) of a registrant. Note that a registration process to register a registration blood vessel formation pattern in the registration database DB is performed by a special registration apparatus or this identification apparatus 1.

Then the identification unit 5 calculates a matching level of a blood vessel formation pattern of blood vessel formation pattern data given from the information creation unit 4 and a registered blood vessel formation pattern being registered in the registration database DB, with a phase cross-correlation function, for example.

If the matching level is a prescribed threshold value or lower, the identification unit 5 identifies the imaging target of the imaging unit 3 of this time as a non-registrant. If the matching level is higher than the prescribed threshold value, the imaging target is identified as a registrant.

By performing the identification process by using a blood vessel formation pattern unique to a body as described above, this identification apparatus 1 can prevent third party's spoofing as well as preventing direct steal from a body, as compared with a case of using fingerprints on a body.

(2) Specific Construction of Imaging Unit

Figure 2:
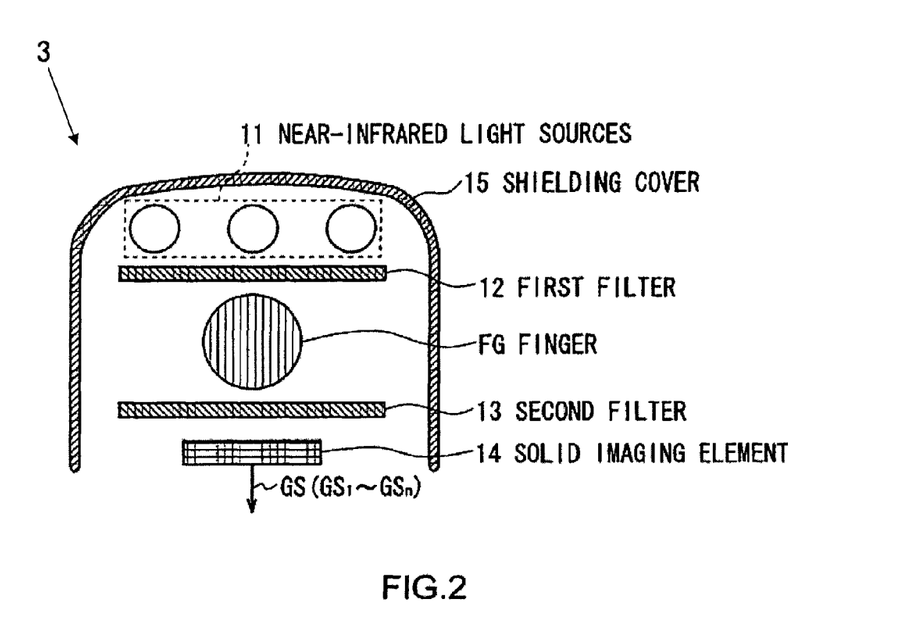
FIG. 2 is a schematic diagram showing a construction of an imaging unit.

Referring to FIG. 2, the imaging unit 3 is equipped with, for example, three near-infrared light sources 11 for emitting near-infrared light. On the light path of the near-infrared light emitted from these near-infrared light sources 11, a first filter 12 for allowing light of a specific near-infrared light bandwidth out of the near-infrared light to pass therethrough, a second filter 13 for allowing light of a near-infrared light bandwidth which is absorbed in the venous blood and its neighboring bandwidths, out of the light arriving through the first filter 12, to pass therethrough, and a solid imaging element 14 are arranged in order.

This imaging unit 3 is designed so that a finger FG can be inserted and fixed between the first filter 12 and the second filter 13. In addition, the imaging unit 3 has a shielding cover 15 for blocking the outside light in the air out of the light path of the near-infrared light, thereby being capable of reducing influences of visible light and ultraviolet light existing outside the shielding cover 15 on the near-infrared light in imaging the blood vessels of the finger FG.

In this case, when receiving an imaging command from the control unit 2 (FIG. 1), the imaging unit 3 emits near-infrared light from the near-infrared light sources 11 to irradiate the finger FG fixed between the first and second filters 12 and 13 with the near-infrared light via the first filter 12.

The near-infrared light is specifically absorbed in intrinsic hemoglobin of the blood vessel tissues of the finger FG and pass through or is reflected by the other tissues. Therefore, the near-infrared light obtained via the finger FG enters the solid imaging element 14 through the second filter 13 as blood vessel pattern light representing the formation pattern of the blood vessel tissues.

Then the imaging unit 3 performs photoelectric conversion on the blood vessel pattern light with the solid imaging element 14, sequentially reads charges being stored in the solid imaging element 14 according to a readout control signal as blood vessel image signals $GS_1, GS_2, \ldots, GS_n$, and sends them to the information creation unit 4 (FIG. 2).

As described above, the imaging unit 3 images the blood vessels of a finger FG to create a plurality of blood vessel images as a result of the imaging.

(3) Specific Construction of Information Creation Unit

Figure 3:
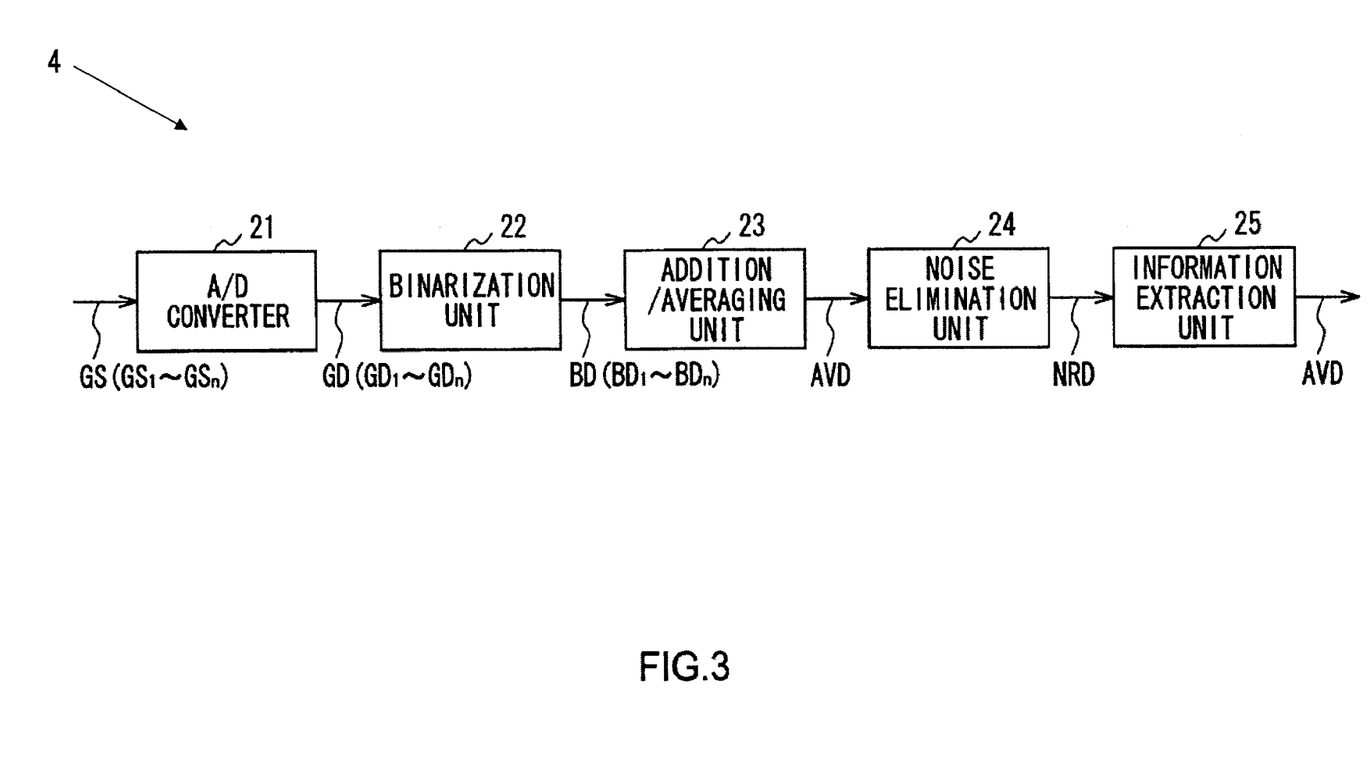
FIG. 3 is a block diagram of an information creation unit.

Referring to FIG. 3, this information creation unit 4 is composed of an analog/digital (A/D) converter 21, a binarization unit 22, an addition/averaging unit 23, a noise elimination unit 24 and an information extraction unit 25.

The A/D converter 21 performs A/D conversion on blood vessel image signals GS ($GS_1$ to $GS_n$) sequentially received from the imaging unit 3 (FIG. 2) and sequentially sends the resultant data (hereinafter, referred to as blood vessel image data GD ($GD_1$ to $GD_n$) to the binarization unit 22.

The binarization unit 22 binarizes the blood vessel image data GD ($GD_1$ to $GD_n$) sequentially received from the A/D converter 21, and sequentially sends the resultant binarized blood vessel image data BD ($BD_1$ to $BD_n$) to the addition/averaging unit 23.

The addition/averaging unit 23 sequentially adds and averages the binarized blood vessel image data BD ($BD_1$ to $BD_n$) received from the binarization unit 22. Specifically, as shown in FIG. 4, the addition/averaging unit 23 adds and averages the corresponding pixels of the binarized blood vessel image data $BD_1$ and $BD_2$, and then adds and averages the corresponding pixels of the addition/averaging result and the binarized blood vessel image data $BD_3$.

The addition/averaging unit 23 sequentially performs the addition and averaging process on the remaining binarized blood vessel image data $BD_4$ to $BD_n$, and sends the final addition/averaging result to the noise elimination unit 24 (FIG. 3) as composed data of the plurality of binarized blood vessel images (hereinafter, referred to as composed binarized blood vessel image data) AVD.

Figure 4:
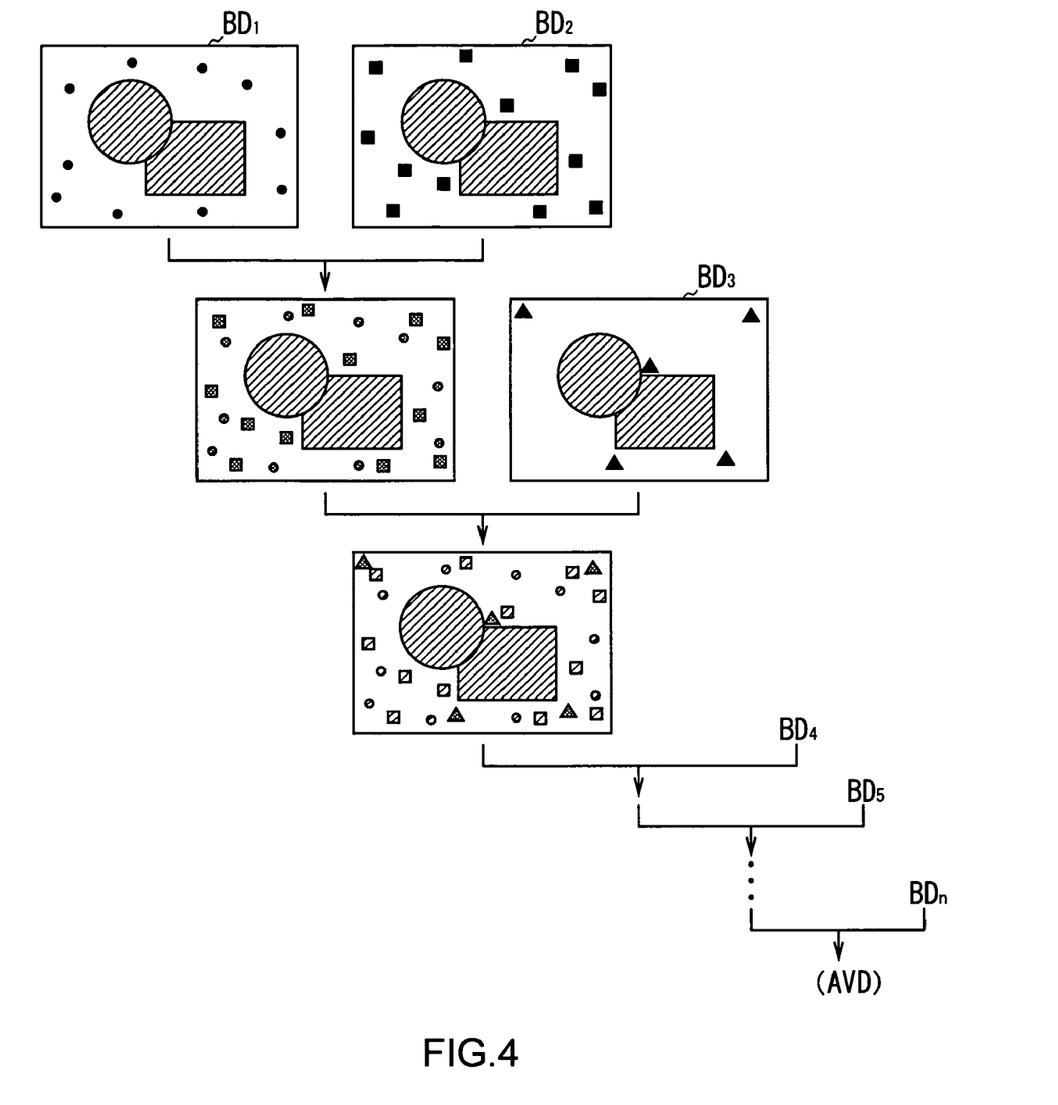
FIG. 4 is a schematic diagram explaining an addition/averaging process.

In this case, as shown in FIG. 4, each addition/averaging process lowers the luminance levels of random noises (hereinafter, referred to as condition noises) which are generated in each binarized blood vessel image of the binarized blood vessel image data BD ($BD_1$ to $BD_n$) due to different near-infrared light passing through or reflected by the tissues other than the blood vessel tissues, different imaging conditions such as an irradiation amount and irradiation strength of near-infrared light, and physiologic change of imaging target. This means that parts corresponding to the noises become blurred in the composed binarized blood vessel image, with the result that the blurred parts merge with the background of the composed binarized blood vessel image, regardless of the different imaging conditions and the physiologic change of imaging target.

As to the blood vessels of the binarized blood vessel images, on the other hand, each addition/averaging process averages the luminance levels of parts which are blurred due to the condition noises. As a result, the blood vessels are highlighted and faithfully represent the actual blood vessels, regardless of the different imaging conditions and the physiologic change of imaging target.

Figure 5A:
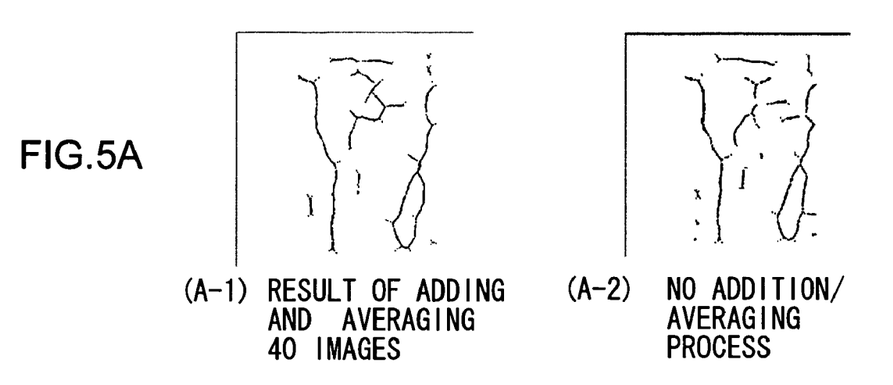
FIGS. 5A and 5B show results of the addition/averaging process.
Figure 5B:
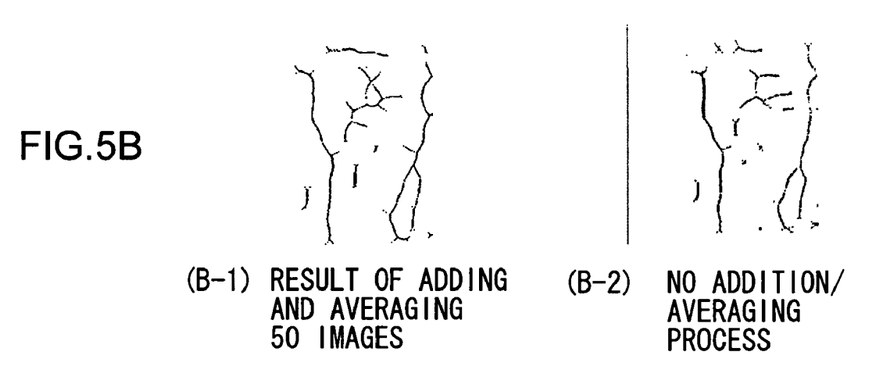

As is clear from experimental results shown in FIGS. 5A and 5B, by sequentially performing the addition/averaging process on a plurality of binarized blood vessel images as described above, the addition/averaging unit 23 can create a composed binarized blood vessel image in which only blood vessels are highlighted, regardless of different imaging conditions and physiologic change of imaging target.

The noise elimination unit 24 (FIG. 3) eliminates a prescribed number or fewer pixels (hereinafter, referred to as target pixels) as condition noises from the composed binarized blood vessel image of the composed binarized blood vessel image data AVD received from the addition/averaging unit 23.

Figure 6:
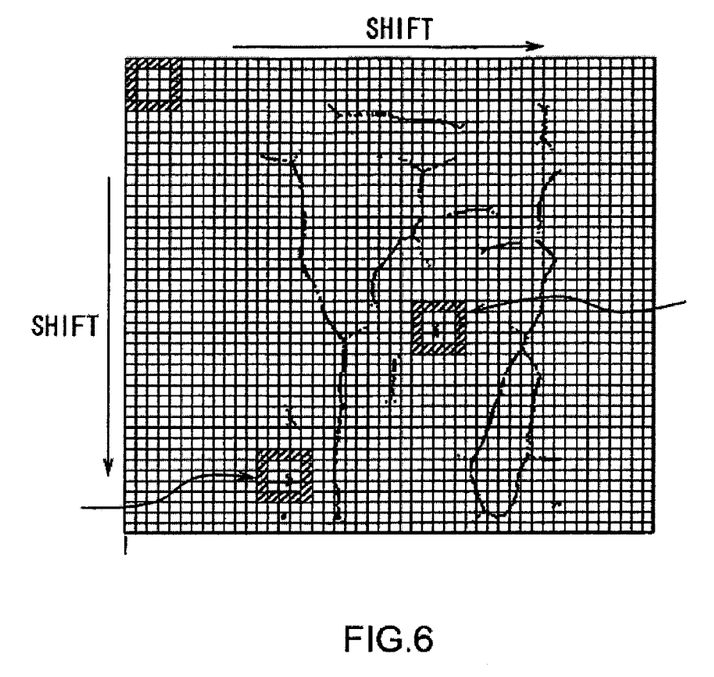
FIG. 6 is a schematic diagram explaining detection and elimination of condition noises.

Specifically, for example, as shown in FIG. 6, the noise elimination unit 24 sequentially extracts an image (hereinafter, referred to as search image) of 5-by-5 pixels (hereinafter, this size is referred to as a search size) to be searched for condition noises, from the composed binarized blood vessel image while shifting the search image one pixel by one pixel in a raster scanning direction.

When the luminance levels of the outer pixels (indicated by hatched lines in FIG. 6) of a search image are all "0" (that is, the outer pixels represent the background), the noise elimination unit 24 detects whether the pixels existing inside the outer pixels include an isolated target pixel which has a luminance level other than "0".

If the noise elimination unit 24 detects a target pixel (indicated by arrows in FIG. 6), this unit 24 assimilates the target pixel as the background by changing its luminance level to "0". This means that the target pixel is eliminated from the composed binarized blood vessel image as condition noises.

By eliminating isolated condition noises from the composed binarized blood vessel image as described above, the noise elimination unit 24 is capable of correctly eliminating condition noises remaining after the addition/averaging process of the addition/averaging unit 23, from the composed binarized blood vessel image.

In addition to the above configuration, every time when the detection and elimination of isolated condition noises from the composed binarized blood vessel image are completed, the noise elimination unit 24 changes the search size of the search image to, for example, 6-by-6 pixels and then to 7-by-7 pixels, which are larger than a previous search size, and starts to examine the composed binarized blood vessel image with a search image of the changed size.

This can correctly eliminate condition noises from the composed binarized blood vessel image even when the condition noise pixels neighbor each other.

In addition, this noise elimination unit 24 counts the number of eliminated target pixels with an internal counter, and only when determining based on the counted number that the blood vessels of the composed binarized blood vessel image can be used for identification, gives this image to the information extraction unit 25.

If the internal counter shows a number greater than a prescribed threshold value (hereinafter, referred to as a noise limit value), the noise elimination unit 24 identifies the blood vessels of the composed blood vessel image as being unusable for identification. In this case, the controller 2 (FIG. 3) notifies the user using the imaging unit 3 via, for example, a display unit (not shown) that he/she should image his/her blood vessels again.

If the number of eliminated target pixels is fewer than the noise limit value when the noise elimination unit 24 finally completes the elimination of the target pixels from the composed binarized blood vessel image with changing the search size, the noise elimination unit 24 sends data (hereinafter, referred to as noise-free blood vessel image data) NRD of the resultant composed binarized blood vessel image (hereinafter, referred to as noise-free blood vessel image) to the information extraction unit 25.

As described above, this noise elimination unit 24 gives the information extraction unit 25 only composed binarized blood vessel images of which the blood vessels are identified based on the number of eliminated target pixels as being usable for identification. This can previously avoid a registrant from being erroneously identified as a third party.

The information extraction unit 25 extracts the blood vessels existing in a specified region, from the noise-free blood vessel image based on the noise-free blood vessel image data NRD received from the noise elimination unit 24. Specifically, the identification information creation unit 4 divides the noise-free blood vessel image into 5 by 5 parts, and extracts the central 3 by 3 parts.

Then the information extraction unit 25 creates a blood vessel formation pattern based on the blood vessels of the 3 by 3 parts as blood vessel formation pattern data BPD, and sends this data BPD to the identification unit 5 (FIG. 1).

As described above, the information creation unit 4 is capable of creating the blood vessel formation pattern data BPD from the plurality of blood vessel images.

(4) Identification Information Creation Process

Figure 7:
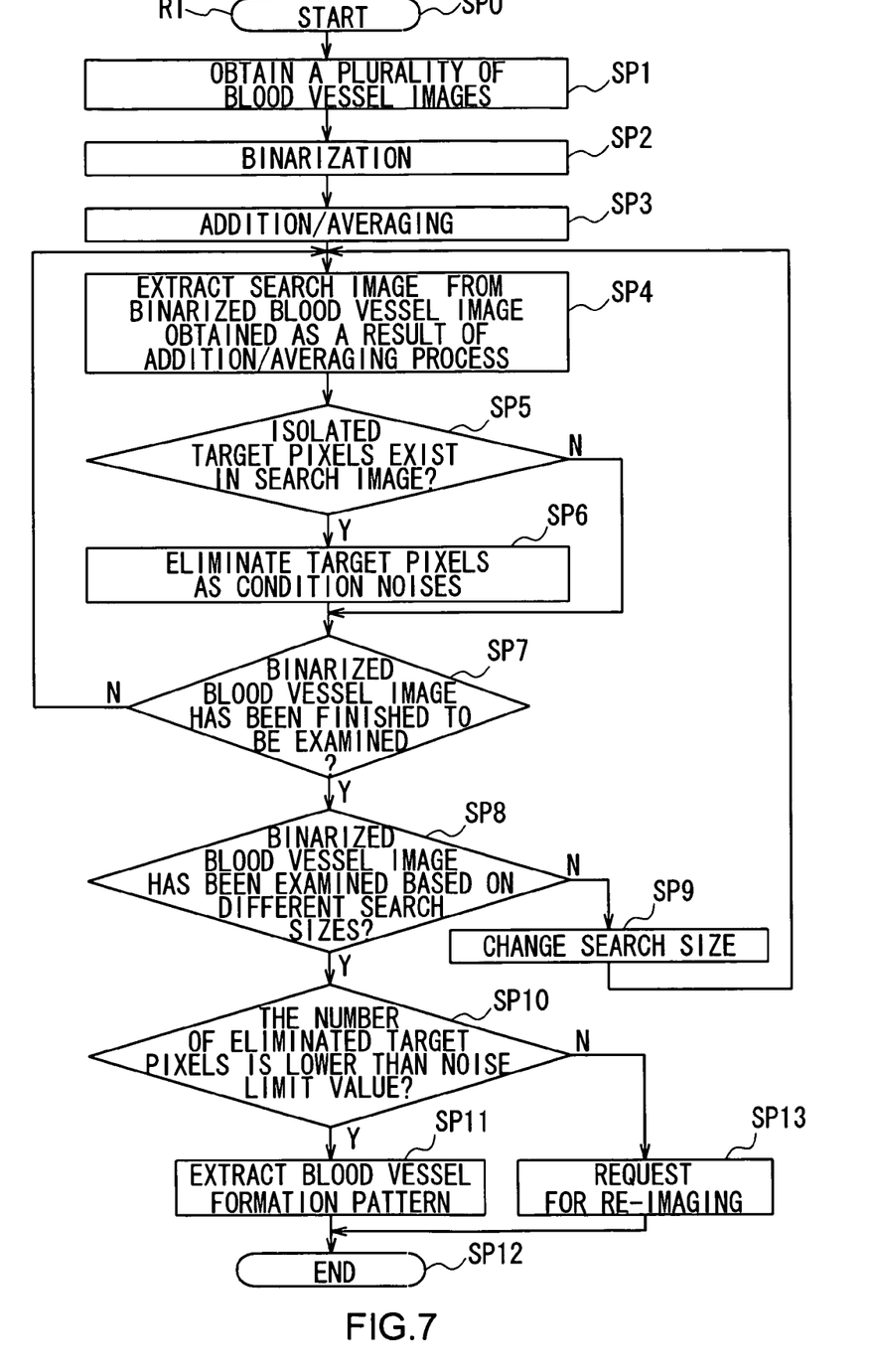
FIG. 7 is a flowchart showing an information creation procedure.

The information creation unit 4 performs the information creation process with an identification information creation procedure RT shown in FIG. 7.

When receiving a process start command from the control unit 2, the information creation unit 4 starts this information creation procedure RT at step SP0. At step SP1, the information creation unit 4 sequentially receives a plurality of blood vessel image signals $GS_1$ to $GS_n$ (FIG. 3) as a result of imaging of the imaging unit 3.

At step SP2, the information creation unit 4 sequentially performs the A/D conversion and the binarization process on the blood vessel image signals GS ($GS_1$ to $GS_n$). At step SP3, the information creation unit 4 performs the addition/averaging process to create composed binarized blood vessel image data AVD (FIG. 3).

At step SP4, the information creation unit 4 extracts the most-left search image from the composed binarized blood vessel image of the composed binarized blood vessel image data AVD. At step SP5, the information creation unit 4 determines whether the luminance levels of the outer pixels (shown by the hatched lines in FIG. 6) of the search image are all "0" and there are isolated target pixels (indicated by the arrows in FIG. 6) inside the outer pixels.

An affirmative result means that target pixels exist only inside the outer pixels. In this case, at step SP6, the information creation unit 4 changes the luminance levels of the target pixels into the luminance level of the background to eliminate the target pixels as condition noises and then goes on to step SP7.

A negative result, on the contrary, means that all of the pixels of the search image represent the background or that the search image has a line representing the blood vessels. In this case, the information creation unit 4 moves on to step SP7.

At step SP7, the information creation unit 4 determines whether the composed binarized blood vessel image has been finished to be entirely examined. If no, the information creation unit 4 returns back to step SP4 and extracts a next search image existing, for example, on the one-pixel right side of the current search image and repeats the above process. If yes, on the contrary, the process goes on to step SP8.

At step SP8, the information creation unit 4 determines whether the composed binarized blood vessel image is finished to be examined based on preset different search sizes. If no, the process goes on to step SP9 and the information creation unit 4 changes the search size to a larger size, returns back to step SP4 and repeats the above process. If yes, on the contrary, the process goes on to next step SP10.

At step SP10, the information creation unit 4 determines whether the number of eliminated target pixels is lower than a noise limit value. An affirmative result here means that the blood vessels of the composed binarized blood vessel image can be used for identification. In this case, the information creation unit 4 moves on to step SP11 to extract a blood vessel formation pattern from the composed blood vessel image and send this to the identification unit 5 as blood vessel formation pattern data BPD (FIG. 3). Then the process moves on to step SP12 to complete this information creation procedure RT.

A negative result, on the contrary, means that the blood vessels of the composed binarized blood vessel image cannot be used with a high possibility. In this case, the information creation unit 4 moves on to next step SP13 to notify the user using the imaging unit 3 that he/she should image the blood vessels again, and moves on to step SP12 to complete this information creation procedure RT.

As described above, the information creation unit 4 can create information with this identification information creation procedure RT.

(5) Operation and Effects of this Embodiment

This identification apparatus 1 images the blood vessels unique to a body and creates a binarized image from the resultant images. Then the identification apparatus 1 eliminates a prescribed number or fewer isolated target pixels as condition noises from the binarized image (FIG. 6), and creates identification information based on the blood vessels of the resultant noise-free binarized image.

As a result, this identification apparatus 1 can reduce a possibility of creating identification information with the condition noises as a part of the blood vessels, thus being capable of preventing the identification information from deteriorating due to different imaging conditions and physiologic change of imaging target.

As a technique to eliminate a prescribed number or fewer isolated target images from a binarized image, this identification apparatus 1 sequentially extracts a search image of a prescribed search size from the binarized image and eliminates isolated target pixels existing inside the outer pixels (indicated by the hatched lines in FIG. 6) of the extracted search image as condition noises.

Therefore, this identification apparatus 1 can prevent an image representing blood vessels, which are used to create identification information, from being eliminated erroneously, thus being capable of further preventing the identification information from deteriorating due to the different imaging conditions and the physiologic change of imaging target.

In addition, before eliminating condition noises, this identification apparatus 1 sequentially performs the addition/averaging process on a plurality of binarized images sequentially obtained as a result of imaging of the imaging unit 3.

As a result, this identification apparatus 1 is capable of creating a binarized image in which only blood vessels are highlighted while parts corresponding to unnecessary condition noises become blurred, thereby being capable of correctly preventing the blood vessels, which are used for creating identification information, from being eliminated as condition noises.

Furthermore, this identification apparatus 1 creates identification information only when the number of eliminated target pixels is lower than the noise limit value. As a result, this identification apparatus 1 can further prevent the identification information from deteriorating due to the different imaging conditions and the physiologic change of imaging target.

According to the above configuration, a prescribed number or fewer isolated target pixels are eliminated as condition noises from a binarized image created from images obtained as a result of imaging the blood vessels unique to a body, and identification information is created based on the blood vessels of the resultant noise-free binarized image. This can reduce a possibility of creating identification information by using condition noises as a part of the blood vessels, thereby being capable of preventing the identification information from deteriorating due to the different imaging conditions and the physiologic change of imaging target and thus improving reliability in the identification process.

(6) Other Embodiments

The above-described embodiment has described a case of applying the imaging unit 3 shown in FIG. 2 as an imaging means for imaging unique components of a body. This invention, however, is not limited to this and an imaging unit having another construction can be applied.

In this case, the blood vessels of a finger are imaged as the unique components. This invention, however, is not limited to this and other unique components can be imaged, such as the blood vessels of all body or an eye, fingerprints or a mouth.

Further, the above-described embodiment has described a case where an elimination means for eliminating a prescribed number or fewer isolated pixels from a binarized image sequentially extracts a search image from the composed binarized blood vessel image while shifting the search image one pixel by one pixel in the raster scanning direction, and when the luminance levels of the outer pixels (indicated by the hatched lines in FIG. 6) of the extracted search image are all "0", eliminates isolated target pixels (indicated by the arrows in FIG. 6) existing inside the outer pixels as condition noises. This invention, however, is not limited to this and another technique can be applied to eliminate the target pixels.

As an example, after pixels (hereinafter, referred to as not-background pixels) of which the luminance levels are not "0" are all detected from a binarized image, a certain pixel out of these not-background pixels is attracted, and the attracted pixel and its surrounding not-background pixels are linked one after another. If the number of the linked not-background pixels is a prescribed number or fewer when there is no more not-background pixel to be linked, the luminance levels of the not-background pixels are changed to the luminance level of the background, thereby eliminating the not-background pixels as condition noises. This technique can also obtain the same effects as the above embodiment.

As another example, in a case where the luminance levels of the outer pixels (indicated by the hatched lines in FIG. 6) of an extracted search image are all "0", a new process can be performed in addition to the process to eliminate isolated target pixels (indicated by the arrows in FIG. 6) existing inside the outer pixels as condition noises.

Figure 9:
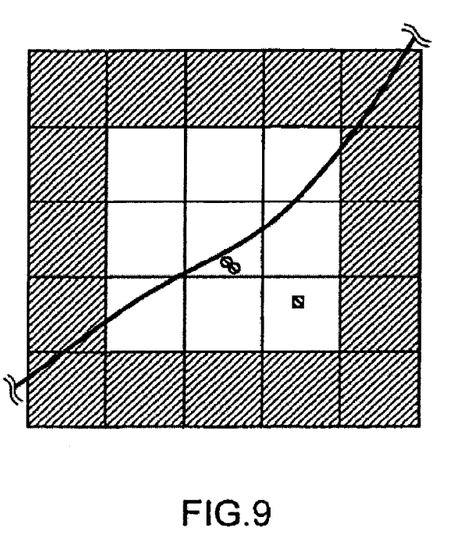
FIG. 9 is a schematic diagram explaining elimination of condition noises according to another embodiment.

Specifically, as shown in FIG. 9, in a case where the luminance level of at least one outer pixel (indicated by the hatched lines in FIG. 6) of a search image is "0", the noise elimination unit 24 detects whether there are target pixels (hereinafter, referred to as an inside target pixel) inside the outer pixels. If one or more inside target pixels are detected, the noise elimination unit 24 calculates the luminance level of each inside target pixel and an average (hereinafter, referred to as outer luminance average) of the luminance levels of the outer pixels with luminance levels other than "0". Note that a composed binarized blood vessel image (addition/averaging result) has highlighted blood vessels and blurred parts corresponding to condition noises. Therefore, if the luminance level of an inside target pixel is lower than the outer luminance average, the inside target pixel can be identified as condition noises. The noise elimination unit 24 eliminates inside target pixels each of which the luminance level has a difference larger than a prescribed value from the outer luminance average.

By doing this, even if the luminance level of any one of outer pixels is not "0", isolated target pixels existing inside outer pixels can be correctly eliminated. In addition, even if a pixel representing blood vessels and a target pixel neighbor each other, the target pixel can be correctly eliminated as condition noises. As a result, identification information can be surely prevented from deteriorating due to the different imaging conditions and the physiologic change of imaging target.

Figure 8A:
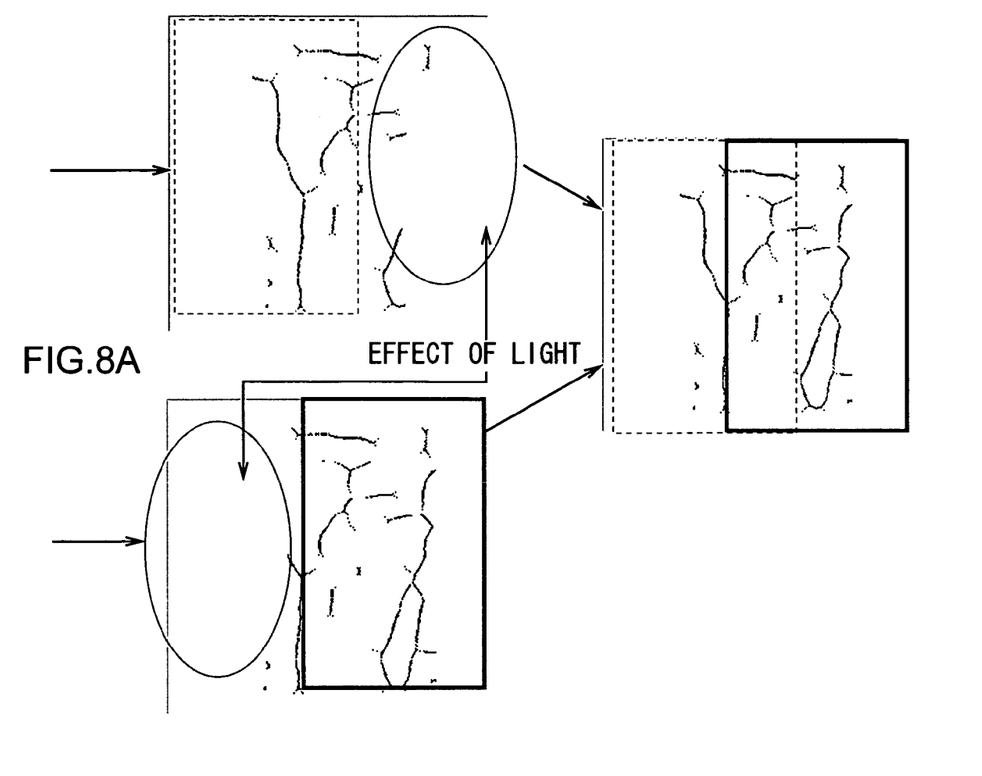
FIGS. 8A and 8B are schematic diagrams explaining composition of images according to another embodiment.
Figure 8B:
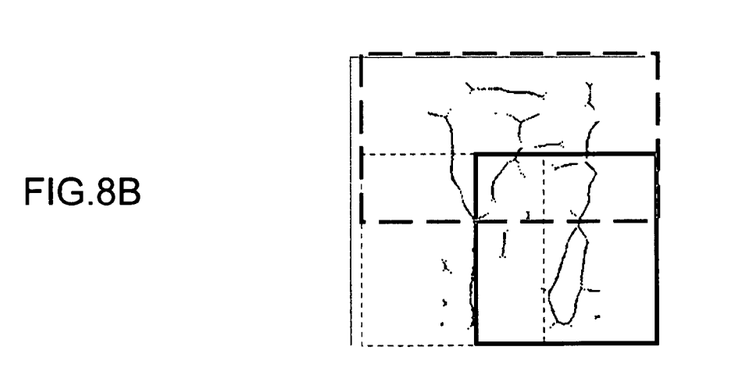

Furthermore, the above-described embodiment has described a case where a composed binarized blood vessel image is created by sequentially performing the addition and averaging process on binaraized images based on a plurality of images sequentially obtained as a result of imaging of the imaging unit 3. This invention, however, is not limited to this and, as shown in FIGS. 8A and 8B, some good images can be extracted from the plurality of images and composed to create a composed binarized blood vessel image.

Furthermore, the above-described embodiment has described a case where a creation means for creating identification information based on unique components of a binarized image creates a blood vessel formation pattern of blood vessels, which is a part of the binarized image, as identification information. This invention, however, is not limited to this and the blood vessel formation pattern of the blood vessels in the binarized image can be created as identification information.

Note that, in this case, another creation technique can be applied depending on unique components.

Furthermore, the above-described embodiment has described a case where the information creation unit 4 shown in FIG. 3 is applied as an information creation apparatus for creating information on a body. This invention, however, is not limited to this and part or all of various processes which are executed by the information creation unit 4 can be made as a program to be run by the control unit 2 of the identification apparatus 1 or the control unit of an electronic devices such as a portable telephone.

This invention can be used for identifying a rightful user of a terminal device such as a personal computer or portable telephone or a device including a household electronic device.

While there has been described in connection with the preferred embodiments of the invention, it will be obvious to those skilled in the art that various changes and modifications may be aimed, therefore, to cover in the appended claims all such changes and modifications as fall within the true spirit and scope of the invention.

What is claimed is:

1. An information creation apparatus for creating information on a body, comprising:
a solid imaging element configured to sequentially capture a plurality of blood vessel images of a same image type based on near-infrared light received from the body;
a binarization unit configured to create a plurality of binarized images from the plurality of blood vessel images sequentially received from the solid imaging element;
a composition unit configured to sequentially perform an averaging process on the plurality of binarized images to create a composed binarized image;
an elimination unit configured to eliminate isolated pixels from the composed binarized image received from the composition unit; and
a creation unit configured to create identification information based on the blood vessels of the composed binarized image subjected to the elimination of the elimination unit, wherein
the elimination unit is configured to eliminate a prescribed number or fewer isolated pixels, to determine whether a number of the isolated pixels eliminated is a prescribed threshold value or lower, and when the number of the isolated pixels eliminated is determined to be the prescribed threshold value or lower, to identify the composed binarized image subjected to the elimination as being usable for creating the information on the body; and
the creation unit is configured to create the identification information based on the blood vessels of the composed binarized image identified by the elimination unit.

2. The information creation apparatus according to claim 1, wherein
the elimination unit is configured to sequentially extract a search image from the composed binarized image and to eliminate the isolated pixels existing inside outer pixels of the search image extracted.

3. The information creation apparatus according to claim 1, wherein
the creation unit is configured to create the identification information based on the blood vessels of the composed binarized image subjected to the elimination of the elimination unit only when the number of the isolated pixels eliminated is determined to be the prescribed threshold value or lower.

4. An information creation method for creating information on a body, comprising:
capturing, by a solid imaging element, a plurality of blood vessel images of a same image type based on near-infrared light received from the body;
creating a plurality of binarized images from the plurality of blood vessel images sequentially received from the solid imaging element;
sequentially performing an averaging process on the plurality of binarized images to create a composed binarized image;
eliminating isolated pixels from the composed binarized image created; and
creating identification information based on the blood vessels of the composed binarized image subjected to the eliminating step, wherein
in the eliminating step, a prescribed number or fewer isolated pixels are eliminated, whether a number of the isolated pixels eliminated is a prescribed threshold value or lower is determined, and when the number of the isolated pixels eliminated is determined to be the prescribed threshold value or lower, the composed binarized image subjected to the elimination is identified as being usable for creating the information on the body; and in the creating the identification information step, the identification information is created based on the blood vessels of the composed binarized image identified in the eliminating step.

5. The information creation method according to claim 4, wherein,
in the eliminating step, a search image is sequentially extracted from the composed binarized image and the isolated pixels existing inside outer pixels of the search image extracted are eliminated.

6. The information creation method according to claim 4, wherein,
in the creating the identification information step, the identification information based on the blood vessels of the composed binarized image subjected to the eliminating step is created only when the number of the isolated pixels eliminated is determined to be the prescribed threshold value or lower.

7. An information creation apparatus for creating information on a body, comprising:
imaging means for capturing a plurality of blood vessel images of a same image type based on near-infrared light received from the body;
binarization means for creating a plurality of binarized images from the plurality of blood vessel images sequentially received from the imaging means;
composition means for sequentially performing an averaging process on the plurality of binarized images to create a composed binarized image;
elimination means for eliminating isolated pixels from the composed binarized image received from the composition means; and
creation means for creating identification information based on the blood vessels of the composed binarized image subjected to the elimination of the elimination means, wherein
the elimination means eliminates a prescribed number or fewer isolated pixels, determines whether a number of the isolated pixels eliminated is a prescribed threshold value or lower, and when the number of the isolated pixels eliminated is determined to be the prescribed threshold value or lower, identifies the composed binarized image subjected to the elimination as being usable for creating the information on the body; and
the creation means creates the identification information based on the blood vessels of the composed binarized image identified by the elimination means.

8. The information creation apparatus according to claim 7, wherein
the creation means creates the identification information based on the blood vessels of the composed binarized image subjected to the elimination of the elimination means only when the number of the isolated pixels eliminated is determined to be the prescribed threshold value or lower.

* * * * *